(12) United States Patent
Nagamune et al.

(10) Patent No.: US 7,501,280 B2
(45) Date of Patent: Mar. 10, 2009

(54) IMMOBILIZED CELLS AND LIPOSOMES AND METHOD OF IMMOBILIZING THE SAME

(75) Inventors: Teruyuki Nagamune, Saitama (JP); Jun Miyake, Osaka (JP); Masato Miyake, Osaka (JP); Koichi Kato, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 391 days.

(21) Appl. No.: 10/506,210

(22) PCT Filed: Feb. 28, 2003

(86) PCT No.: PCT/JP03/02340

§ 371 (c)(1),
(2), (4) Date: Oct. 14, 2004

(87) PCT Pub. No.: WO03/074691

PCT Pub. Date: Sep. 12, 2003

(65) Prior Publication Data

US 2005/0106721 A1      May 19, 2005

(30) Foreign Application Priority Data

Mar. 1, 2002    (JP)    ............................. 2002-055459

(51) Int. Cl.
*C12N 5/02* (2006.01)
*C12N 5/06* (2006.01)
(52) U.S. Cl. ...................................... 435/325; 435/402
(58) Field of Classification Search ...................... None
See application file for complete search history.

(56) References Cited

U.S. PATENT DOCUMENTS

| | | | |
|---|---|---|---|
| 5,185,415 A | | 2/1993 | Kawabata et al. |
| 5,932,462 A | * | 8/1999 | Harris et al. ................. 435/188 |
| 6,329,209 B1 | * | 12/2001 | Wagner et al. ............... 436/518 |
| 6,656,906 B1 | * | 12/2003 | Barney et al. ................. 514/12 |

FOREIGN PATENT DOCUMENTS

| | | |
|---|---|---|
| EP | 408292 | 1/1991 |
| EP | 1283257 | 2/2003 |
| JP | 63-196285 | 8/1988 |
| JP | 5-325570 | 12/1993 |
| JP | 7-178 | 1/1995 |
| JP | 07-000178 | * 1/1995 |
| JP | 7-39376 | 2/1995 |
| JP | 8-317785 | 12/1996 |
| JP | 10-180280 | 7/1998 |
| JP | 2001-120267 | 5/2001 |
| JP | 2002-292384 | 10/2002 |
| WO | 92/09267 | 6/1992 |

OTHER PUBLICATIONS

Lemieux et al., J Drug Target. 2000;8(2):91-105.*

(Continued)

*Primary Examiner*—Gary B Nickol
*Assistant Examiner*—Cherie M. Woodward
(74) *Attorney, Agent, or Firm*—Wenderoth, Lind & Ponack, L.L.P.

(57) ABSTRACT

In an inexpensive and convenient method for immobilizing a suspension cell, a phospholipid vesicle or the like regardless of the type of cell, on the surface of a solid phase, a cell is immobilized by causing the cell to contact a support having a hydrophobic chain and a hydrophilic chain.

2 Claims, 15 Drawing Sheets

OTHER PUBLICATIONS

J. Ziauddin et al., "Microarrays of cells expressing defined cDNAs", Nature, 411, pp. 107-110, 2001.

Kohei Umezawa et al., "Position-controlled immobilization of suspension cells for Cell Microarray technology", Seikagaku, vol. 74, No. 8, p. 1094, 4P-789, Aug. 25, 2002.

Koichi Kato et al., "Anchor-ring method of suspension cells to solid phase for Cell Microarray technology", The Society of Chemical Engineers, Japan dai 67 nenkai Kenkyu Happyo Koen Yoshishu, p. 719, P208, Mar. 1, 2002.

* cited by examiner

A

B

A

B

A					B

A B C

IMMOBILIZED CELLS AND LIPOSOMES AND METHOD OF IMMOBILIZING THE SAME

TECHNICAL FIELD

The invention of this application relates to an immobilization material in which a cell and a liposome are immobilized on a support and a method for immobilizing the same. More particularly, the invention of this application relates to a novel immobilization material capable of immediately immobilizing a cell and a liposome and a convenient and highly versatile method therefor.

BACKGROUND ART

In recent years, an enormous amount of gene information is being revealed by genome analysis. In addition, the function of a gene and the relationship between gene information and a protein have also begun to be analyzed, and based on these findings, cell devices such as a sensor for trace amount analysis and a microreactor, which utilize the function of cells or microorganisms, have been actively studied.

Meanwhile, it has been known for a long time that a cell can construct a three-dimensional structure varying according to region, and studies on the ability of cells to form tissue of such high order have been progressing recently. If the mechanism of high order tissue formation of cells is elucidated and the reproduction or control thereof becomes possible, it will be possible to produce various kinds of replacement tissues with a higher biocompatibility than artificial tissues or artificial organs made from a conventional synthetic material, and therefore it also is drawing attention as a technique for organ transplantation.

In addition, recently hematopoietic stem cell transplantation method has attracted attention as a therapeutic method of cancers or leukemias; however, the available amount of hematopoietic stem cells is extremely small, therefore, techniques of large scale hematopoietic stem cell proliferation are being studied.

With regard to the above mentioned construction of cell devices, elucidation of the mechanism of the high order tissue formation of cells, and techniques of hematopoietic stem cell proliferation, etc., it is important to immobilize cells at a high density, and various methods for this have been proposed.

For example, a method which has been known for a long time involves immobilizing adherent cells on a support. Recently, a technique of limiting the adhesion region of cells with the use of a support to which adherent cells cannot adhere, or a support which has been treated so that adherent cells cannot adhere thereto and then making a microarray has been reported. For example, in Shuguang Zhang et al., *Biomaterials* 20, 1213-1220, 1999, it has been reported that by immobilizing a polyethylene glycol (PEG) and a PEG-cell adhesion peptide on the surface with gold foil intermediated by thiol, cells come to adhere to the region on which PEG-cell adhesion peptide has been immobilized without adhering to the region where PEG has been immobilized. In addition, in Junaid Ziauddin et al., *Nature* 411 (6833) 107-110, 2001, it has been reported that a mixed solution of DNA and gelatin is spotted in an array on a glass slide, and when adherent cells are added thereon and contact with it, cells incorporate genes present where the binding of cells to gelatin has taken place, and thereby an array of transient gene expressing cells can be formed.

However, the methods for immobilizing cells as above are all for adherent cells having the property that they adhere to a hydrophobic support or a collagen coated support, and the fact is that there are almost no known methods for immobilizing blood cells, hematopoietic stem cells, floating cells such as certain kinds of cancer cells, bacteria, phospholipid endoplasmic reticula, or the like.

If a highly versatile technique for immobilizing floating cells or bacteria in a living state is established, its usefulness in medical treatment and research would be high.

In addition, in regenerative medicine for skin or the like, to a scaffold or coating of collagen or the like, a method for immobilizing adherent cells has been applied. However adhesion and proliferation takes a long time, and furthermore, it is difficult to immobilize cells against gravitational force.

Accordingly, the invention of this application has taken the above situation into account and makes it an object to solve the problems of conventional techniques, providing an immobilization material in which, regardless of the type of cell, a floating cell, a bacterium, a phospholipid endoplasmic reticulum, or the like is immobilized on the surface of a solid phase, and to provide an inexpensive and convenient immobilization method for obtaining the same.

DISCLOSURE OF THE INVENTION

To solve the foregoing problems, the invention of this application firstly provides a cell immobilization material characterized in that a cell is immobilized on a support having a hydrophobic chain and a hydrophilic chain.

Also, the invention of this application secondly provides the foregoing cell immobilization material characterized in that the support has an immobilizing agent bound to the main body of the support.

Thirdly, the invention of this application provides the cell immobilization material according to either of the above, in which the immobilizing agent is a compound formed by binding a hydrophobic chain and a hydrophilic chain.

The invention of this application provides fourthly the cell immobilization material, in which the hydrophobic chain in the immobilizing agent is at least one kind selected from the group consisting of a saturated or unsaturated hydrocarbon chain which may have a substituent, a lipid which is a constituent of a cell membrane and a complex lipid chain, and fifthly the cell immobilization material, in which the hydrophobic chain in the immobilizing agent is at least one kind selected from the group consisting of a saturated or unsaturated hydrocarbon chain whose carbon number is in a range of 6 to 22.

Also, the invention of this application sixthly provides the cell immobilization material, in which the hydrophilic chain in the immobilizing agent is at least one kind selected from the group consisting of a protein, an oligonucleotide, a polymer or a copolymer of respective derivatives of glycolic acid, lactic acid and p-dioxane, an oligopeptide, a polypeptide, a polyamide, a polyalkylene glycol and a polysaccharide.

Further, the invention of this application provides seventhly the cell immobilization material, in which the hydrophilic chain in the immobilizing agent is a polyethylene glycol, and eighthly the cell immobilization material, in which the hydrophilic chain in the immobilizing agent has a functional group, and ninthly the cell immobilization material, in which the hydrophilic chain in the immobilizing agent has an active ester group at the end.

Further, tenthly, the invention of this application provides the cell immobilization material, in which the immobilizing agent is polyethyleneoxide-oleyl ether-N-hydroxysuccinimide ester.

The invention of this application eleventhly provides the cell immobilization material according to any one of the foregoing second to tenth inventions, in which the cell immobilization material is characterized in that the immobilizing agent is fixed to the main body of the support, intermediated by a immobilizing agent-binding substanceadsorbed to the main body of the support, and twelfthly provides the cell immobilization material, in which the immobilizing agent-binding substance is at least one kind of a protein, a peptide, a silane coupling agent, a polymer having a functional group.

The invention of this application thirteenthly provides the cell immobilization material according to any one of the foregoing, characterized in that a gene is introduced thereinto.

Further fourteenthly, the invention of this application provides a method for forming the cell immobilization material according to any one of the foregoing first to twelfth inventions, in which a cell immobilization method is characterized in that a cell is immobilized by causing a cell to contact a support having a hydrophobic group and a hydrophilic group.

The invention of this application fifteenthly provides the method for forming the cell immobilization material according to the foregoing thirteenth invention, in which a method for introducing a gene into the cell immobilization material is characterized in that immobilization is performed by contacting a gene-containing solution with the support having a hydrophobic group and a hydrophilic group, drying out and solidifying the support, and causing a cell to contact the support.

Also, the invention of this application sixteenthly provides a solid phase culture method for a cell characterized in that a cell is cultured by contacting a medium for culture with the cell immobilization material according to any one of the foregoing.

The invention of this application seventeenthly provides a liposome immobilization material characterized in that a liposome is immobilized on a support having a hydrophobic chain and a hydrophilic chain, and eighteenthly provides the liposome immobilization material characterized in that the support has an immobilizing agent bound to the main body of the support.

The invention of this application nineteenthly provides the liposome immobilization material, in which the immobilizing agent is a compound formed by binding a hydrophobic chain and a hydrophilic chain, and twentiethly provides the liposome immobilization material, in which the hydrophobic chain in the immobilizing agent is at least one kind selected from the group consisting of a saturated or unsaturated hydrocarbon chain which may have a substituent, a lipid forming part of a cell membrane and a complex lipid chain, and twenty-firstly provides the liposome immobilization material, in which the hydrophobic chain in the immobilizing agent is at least one kind selected from the group consisting of a saturated or unsaturated hydrocarbon chain whose carbon number is in a range of 6 to 22.

Twenty-secondly, the invention of this application provides the liposome immobilization material, in which the hydrophilic chain in the immobilizing agent is at least one kind selected from the group consisting of a protein, an oligonucleotide, a polymer or a copolymer of respective derivatives of glycolic acid, lactic acid and p-dioxane, an oligopeptide, a polypeptide, a polyalkyamide, a polyalkylene glycol and a polysaccharide.

Further, the invention of this application provides twenty-thirdly the liposome immobilization material, in which the hydrophilic chain in the immobilizing agent is a polyalkylene glycol, and twenty-fourthly the liposome immobilization material, in which the hydrophilic chain in the immobilizing agent has a functional group, and twenty-fifthly the liposome immobilization material according to any one of the foregoing, in which the hydrophilic chain in the immobilizing agent has an active ester group at the end.

The invention of this application twenty-sixthly provides the foregoing liposome immobilization material, in which the immobilizing agent is polyethyleneoxide-oleyl ether-N-hydroxysuccinimide ester.

And, the invention of this application twenty-seventhly provides the liposome immobilization material according to any one of the foregoing eighteenth to twenty-sixth inventions, in which the liposome immobilization material is characterized in that the immobilizing agent is fixed to the main body of the support, intermediated by a immobilizing agent-binding substance adsorbed to the main body of the support, and twenty-eighthly provides also the liposome immobilization material, in which the immobilizing agent-binding substance is at least one kind of a protein, a peptide, a silane coupling agent, a polymer having a functional group.

Further, the invention of this application twenty-ninthly provides a method for forming the liposome immobilization material according to any one of the foregoing, in which a liposome immobilization method is characterized in that a liposome is immobilized by contacting a liposome with a support having a hydrophobic group and a hydrophilic group.

BEST MODE FOR CARRYING OUT THE INVENTION

In the invention of this application, by "immobilization of a cell and a liposome" is meant binding a cell or a liposome to a support through, for example, an immobilizing agent. The immobilization method of the invention of this application is to immobilize a cell or a liposome by binding an immobilizing agent to a support, for example, the main body of a support, then contacting a cell or a liposome with the obtained support bound with the immobilizing agent.

Note that, in the invention of this application, "cell" generally refers to a "floating cell" (for example, blood cells) which does not adhere to or spread on the surface of a support such as a culture tool and is grown in a state of suspension or precipitate, an "adherent cell" which adheres to and spreads on the surface of a support, and which has been made to float temporarily by dispersing an from the support with an appropriate dispersant such as EDTA-trypsin or dispase (for example, a fibroblast cell detached from a support with an EDTA solution), or a cell adhering to a support. In addition, it also includes a living organism having phospholipid bilayer membrane on the surface such as a bacterium, a virus, an organelle, or of a plant cell (protoplast) from which the cell wall has been removed. In the invention of this application, "liposome" includes an endoplasmic reticulum having phospholipid membrane as well as a living organism. Inside the phospholipid membrane, various substances may be incorporated. Namely, in the immobilization method of the invention of this application, not only a floating cell, for instance a cell which has been made to float temporarily, can be immobilized on a support, but also a cell adhering to a support can be immobilized on another support intermediated by a cell immobilizing agent, or a phospholipid vesicle of something other than an organism and a cell can be simultaneously immobilized on the same support.

Figure 1:
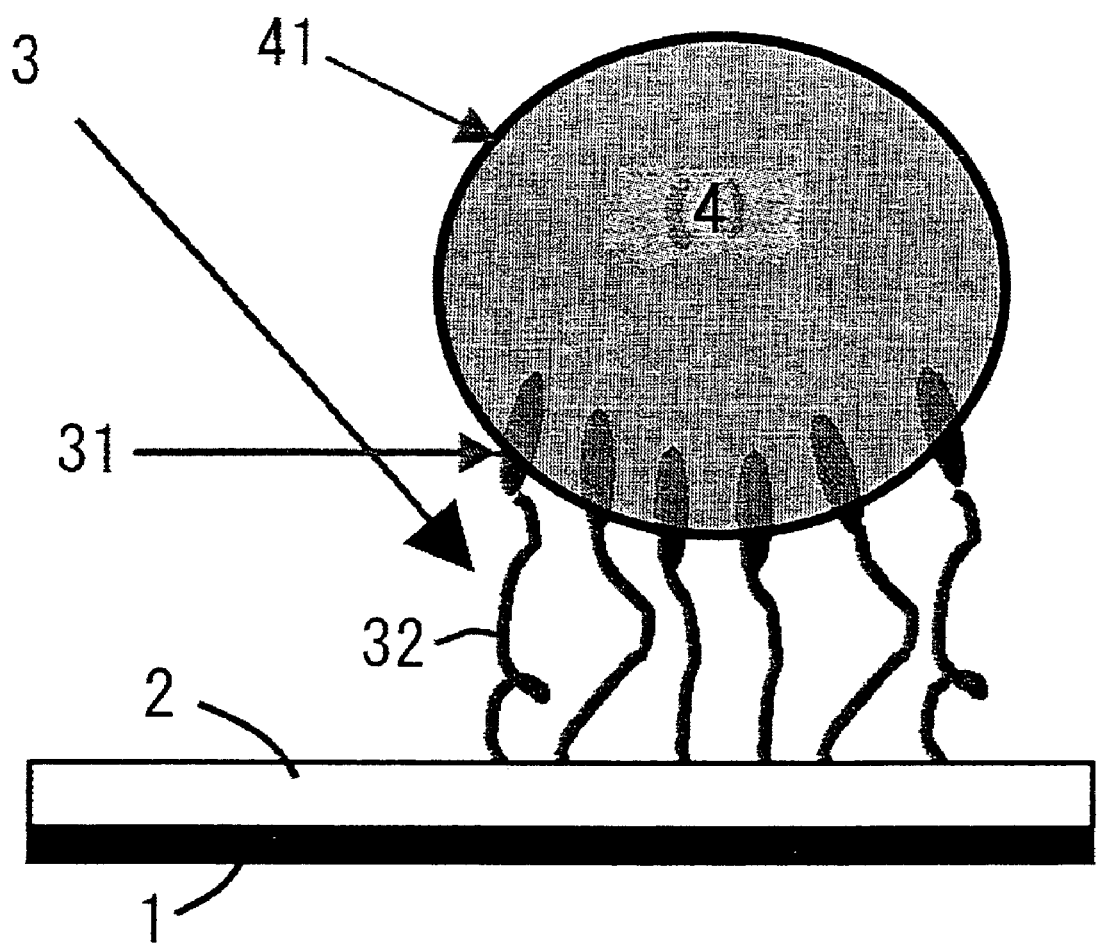
FIG. 1 is a schematic diagram showing the concept of a method for immobilizing a cell and a liposome of the invention of this application (1: main body of support, 2: binding substance, 3: immobilizing agent, 31: hydrophobic chain, 32: hydrophilic chain, 4: cell or liposome, 41: cell membrane or phospholipid membrane).

FIG. 1 shows the concept of the method for immobilizing a cell and a liposome of the invention of this application. First, in the invention of this application, an immobilizing agent (3) is bound to the surface of the main body of a support (1). At this time, the main body of the support (1) is not liquid nor gas, but a substance that can be manipulated by the researcher, and may be anything as long as it is insoluble in a solution in which a cell can coexist. Examples include a plastic, a resin, a polymer, an organic substance, a glass, a metal and the like. The main body of such a support (1) may be in a basal plate form, a colloidal form or a granular form.

In the immobilization method for a cell and a liposome of the invention of this application, in the case where the main body of a support (1) has a functional group capable of binding to an immobilizing agent (3), the immobilizing agent (3) is directly bound to the main body of the support (1). On the other hand, in the case where the main body of a support (1) does not have a functional group capable of binding to an immobilizing agent (3), it suffices that the immobilizing agent (3) and a binding substance (2) which has such a functional group physically adsorb to the surface of the main body of the support (1), and to have this binding substance (2) and the immobilizing agent (3) chemically bound to each other.

At this time, examples of the main body of the support (1) include a silicon chamber, a glass plate, an acrylic plate. Also, as the binding substance (2), bovine serum albumin (BSA), ovalbumin, collagen or the like can be used. Further, it suffices that the immobilizing agent (3) is a compound capable of binding to the main body of the support (or the binding substance (2)) and cell membrane (or phospholipid membrane) (41), and specifically, it is represented as a compound having a hydrophobic chain (31) and a hydrophilic chain (32).

The hydrophobic chain (31) may be either a single chain or plural chains, and it is selected from a saturated or unsaturated hydrocarbon chain which may have a substituent or a complex lipid chain as needed. Examples include a saturated or unsaturated hydrocarbon chain whose carbon number is in a range of 6 to 22, and a saturated alkyl group such as a myristyl group (C14), a palmityl group (C16) or a stearyl group (C18), an unsaturated hydrocarbon such as an oleyl group ($CH_3(CH_2)_7CH=CH(CH_2)_8$) and the like are exemplified. Among them, the one whose carbon number is 14 to 18 including a linol group, a linoleil group and the like is preferably exemplified. Furthermore, a phospholipid is exemplified. These hydrophobic chains may further have a hetero atom such as N, S, O or the like, or a substituent. Among them, an oleyl group which is part of a phospholipid forming part of a biological membrane is preferable.

Meanwhile, the hydrophilic chain (32) is selected from among a protein, an oligopeptide, a polypeptide, a polyacrylamide, a polyethylene glycol and a polysaccharide such as dextran, or a polymer or a copolymer of a glycolic acid derivative, a lactic acid derivative or a p-dioxane derivative. Among them, a polyethylene glycol (PEG) has biocompatibility and is preferable. Such a hydrophilic chain (32) may further have a functional group or may be chemically modified. For example, it may be bound to succinic acid at the end to form a carboxyl group, or have an active ester group such as N-hydroxysuccinimide (NHS). In this way, by chemically modifying the hydrophilic chain (32), it becomes possible to control the connectivity between the immobilizing agent (3) and the main body of the support (1), or between the immobilizing agent (3) and the binding substance (2).

From these, in the invention of this application, preferable examples of a compound as the immobilizing agent (3) include polyethyleneoxide-oleyl ether-N-hydroxy-succinimide ester represented by the following formula (I).

intermediated by the binding substance (2), the binding substance (2) may be the one having a functional group capable of binding the hydrophilic chain (32) of the immobilizing agent (3). For example, a substance having an amino group, a carboxyl group, a thiol group, a hydroxyl group, an aldehyde group or the like is considered.

In the method for immobilizing a cell and a liposome of the invention of this application as above, a cell or a liposome (4) is immobilized by binding the hydrophilic chain (32) of an immobilizing agent (3) to the surface of the main body of a support (1) with or without intermediation of a binding substance (2), and by incorporating the hydrophobic chain (31) of the immobilizing agent (3) into the cell membrane or phospholipid membrane (41).

Of course, it goes without saying that, in the invention of this application, the main body of the support (1) itself may have a hydrophobic chain and a hydrophilic chain. In this case, an immobilizing agent itself does not need to be used.

Figure 2:
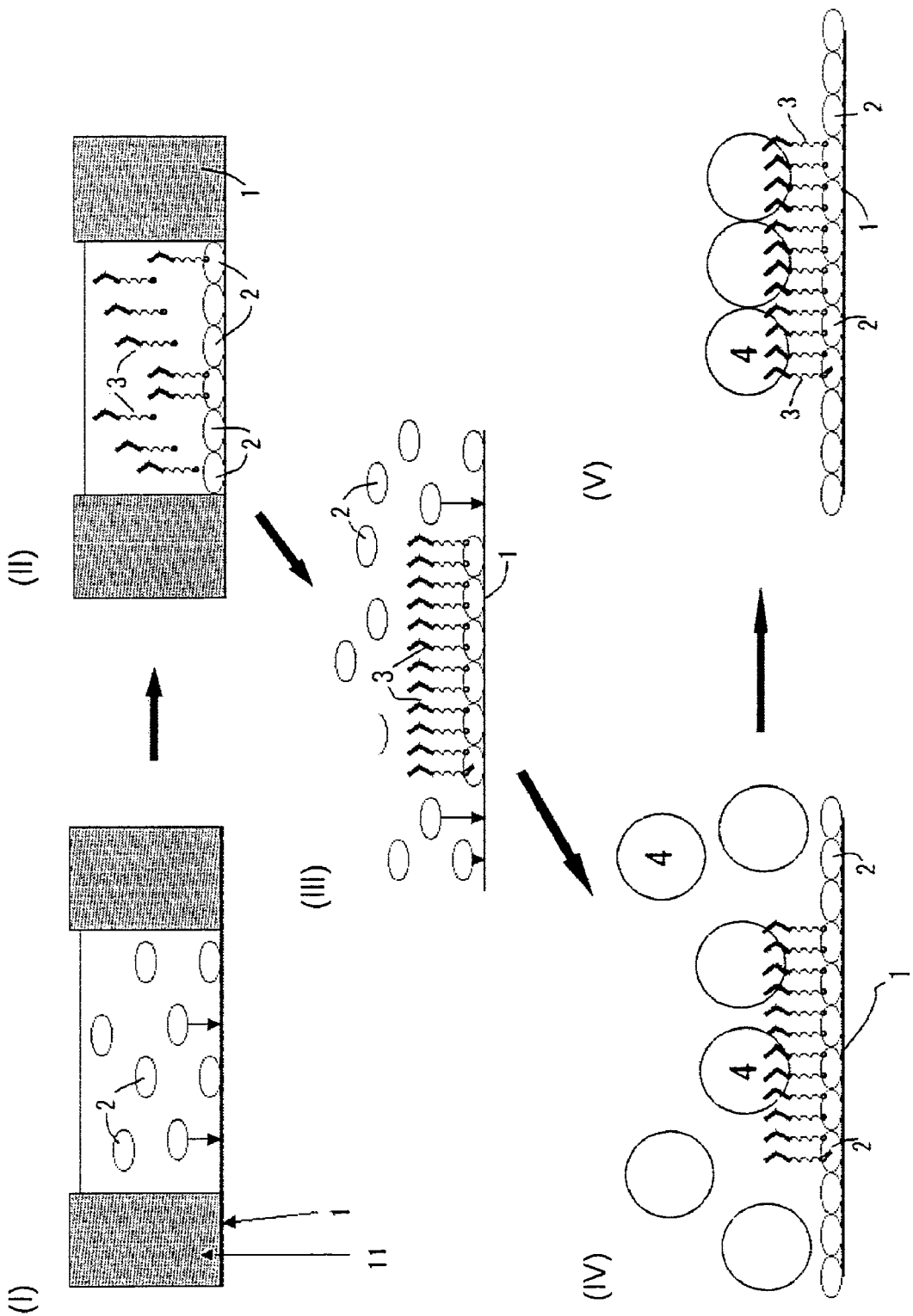
FIG. 2 is a schematic diagram illustrating the procedure of a method for immobilizing a cell and a liposome of the invention of this application (1: main body of support (culture dish), 11: silicon chamber, 2: binding substance (BSA), 3: immobilizing agent (Oleyl-O-PEG-NHS), 31: hydrophobic chain, 32: hydrophilic chain, 4: cell or liposome, 41: cell membrane or phospholipid membrane).

With regard to the method for immobilizing a cell and a liposome of the invention of this application as above, the procedure is illustrated in FIG. 2. Of course, the method for immobilizing a cell and a liposome of the invention of this application is not limited to the one shown in FIG. 2 or the one shown in the following, and various embodiments are possible.

(I) First, a culture dish (1) is introduced into a silicon chamber (11) or the like, bovine serum albumin (BSA) (2) and phosphate buffered saline (PBS) are added thereto, and it is left at 4 to 37° C. for 10 minutes to 48 hours, whereby BSA (2) is physically adsorbed to the surface of the culture dish (1) (at this time, as the culture dish (1), a commercially available one which is made of glass, polystyrene or the like can be used). After the surface of the culture dish is washed several times with PBS, (II) a PBS solution of Oleyl-O-PEG-NHS (3) of 3 μM or more (for example, up to 100 mM) is added and left at room temperature for about 30 seconds to 1 hour (at this time, for the purpose of dissolving Oleyl-O-PEG-NHS (3), a small amount of an organic solvent may be contained in the PBS

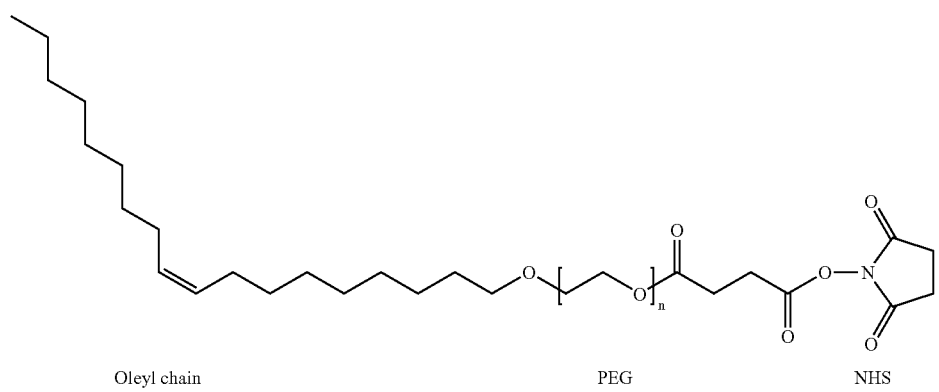

(I)

Oleyl chain          PEG          NHS

However, at this time, the molecular weight of PEG is not limited. In addition, as the unit number of the oxyalkylene chain, the one with 3 to 500 is exemplified. It is more preferably 8 to 300, further more preferably about 12 to 200, whereby a cell and a liposome is rigidly and stably immobilized.

Also, as mentioned above, in the case where the immobilizing agent (3) is bound to the main body of the support solution). The obtained Oleyl-O-PEG immobilization support can be stored in a solution or be stored after drying.

(III) According to need, a PBS/PBS solution is further added, and left at room temperature for about 10 minutes or more and up to 3 hours, whereby the region where Oleyl-O-PEG-NHS (3) was not bound is blocked with BSA (2) (at this time, if PEG-NHS is further added, non-specific adsorption of cells (4) can be inhibited. (Shunguang Zhang et al., Biomaterials, Vol. 20, 1213-1220, 1999)).

(IV) Cells (4) are suspended in PBS or a serum-free culture solution and added to the culture dish (1), then left to stand at room temperature until the cells are precipitated on the bottom face (for example, for about 1 to 15 minutes).

(V) According to need, the culture dish (1) is washed with PBS, whereby a cell immobilization support, in which cells (4) are immobilized on the support (1) intermediated by Oleyl-O-PEG-NHS (3) and BSA (2) is obtained.

In the invention of this application, a cell immobilization material into which an arbitrary gene has been introduced is provided. Such a cell immobilization material can be obtained by binding an immobilizing agent (3) to the surface of the main body of a support (1) with or without intermediation of a binding substance (2) by the foregoing method, putting this in contact with a solution containing a gene, and putting a cell (4) in contact by the foregoing method. At this time, as the solution containing a gene, a commercially available reagent for gene introduction can be used. However, the gene introduction method of the invention of this application is different from a conventional method for introducing a gene into a cell in that after a immobilizing agent (3) is bound with or without intermediation of a binding substance (2), a reagent for gene introduction is added, and it is dried out and solidified, then a cell (4) is brought into contact thereon. By such a method, it becomes possible for a cell to incorporate a gene while preventing a gene from dispersing, and therefore an array of gene expressing cells obtained by immobilizing cells, into which various genes have been introduced on specific locations with a desired size (for example, 100 μm² to 1 mm²) can be prepared. Accordingly, with the use of the cell immobilization material into which a gene has been introduced of the invention of this application, it is possible to make a cell-based microarray, whose application has been limited to adherent cells, of floating cells, and characteristics of the various introduced genes can be analyzed through their expression in the respective cells.

The invention of this application further provides a solid phase culture method for culturing cells which has been immobilized by the above method. In such a solid phase culture method, it becomes possible to grow an immobilized floating cell in an immobilized state under normal conditions. Accordingly, for example, it becomes possible to perform gene expression or the functional analysis thereof in a state where an immobilized cell is alive, with the use of the cell immobilization material into which an arbitrary cell is introduced by the foregoing method.

Hereunder, the invention of this application will be explained in more detail by showing Examples. Of course, the invention of this application is not limited to the following Examples, and it is without saying that various embodiments are possible.

EXAMPLES

In the following Examples, Oleyl-O-PEG-NHS and PEG-NHS both of which had been supplied by Nippon Oil & Fats Co., Ltd. were used.

1. Immobilization of Floating Cells and Adherent Cells.

Example 1

(1) Preparation of Oleyl-O-PEG Immobilization Support

To a polystyrene culture dish, an appropriate amount of an aqueous solution of 1% bovine serum albumin (BSA (fatty acid free, low endotoxin; Sigma))/phosphate buffered saline (PBS (GIBCO)) was added and left at 37° C. for 3 hours so as to adsorb BSA to the culture dish. The culture dish was washed with PBS several times and a PBS solution (100 μM) of Oleyl-O-PEG (4000)-NHS (PEG Mw:4000 Da, n=90) represented by the chemical formula (I) was added and reacted at room temperature for 1 hour.

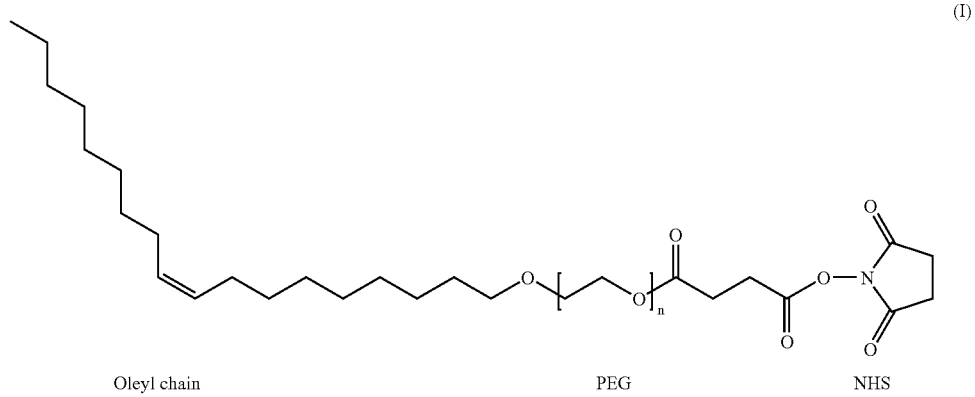

(I)

Oleyl chain     PEG     NHS

The culture dish was further washed with PBS several times, and an Oleyl-O-PEG (4000) binding support was obtained.

The obtained support was stored in a solution at 4° C. or stored after drying until they were used.

(2) Immobilization of Cells

Suspension cells (mouse myeloid 32D) of cell density $1 \times 10^6$ cells/ml were suspended in a serum-free medium (RPMI1640 (Nissui Pharmaceutical Co., Ltd.)) and an appropriate amount thereof was added to the Oleyl-O-PEG (4000) binding support obtained in (1) and left to stand at room temperature for about 15 minutes until the cells precipitated on the surface of the solid phase.

The solid phase was washed with PBS again and cells in the non-binding region of the Oleyl-O-PEG (4000) were removed.

(3) Confirmation of Cell Immobilization

The cells were stained with Calcein AM and the immobilization of cells was confirmed by transmission microscopy and fluorescence microscopy. Further, after the immobilized cells were treated with 70% EtOH and the cells were killed, they were stained with Calcein AM and the cells were similarly observed by microscopy.

Figure 3:
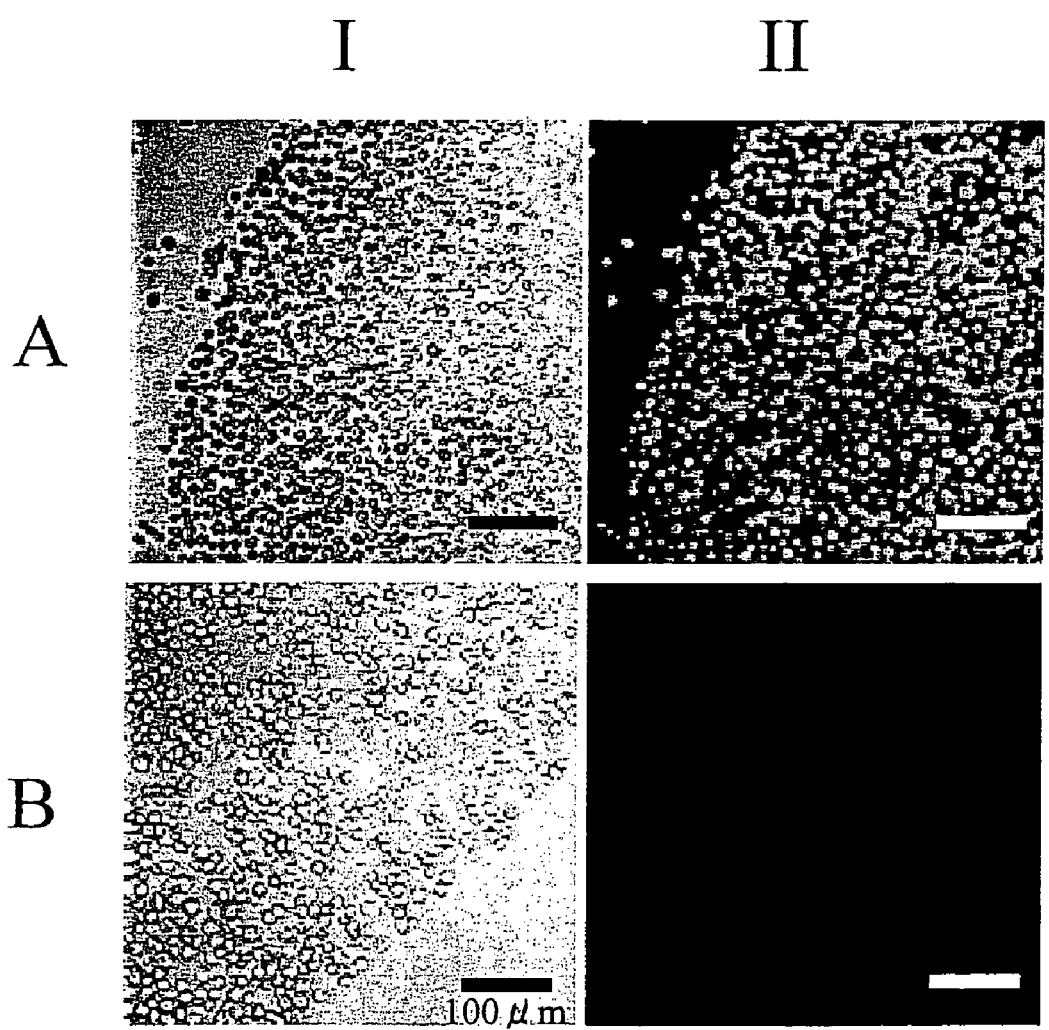
FIG. 3 shows photographs showing images of transmission microscopy and fluorescence microscopy of 32D cells immobilized by the method of the invention of this application and 32D cells killed by treating with 70% EtOH, both of which were stained with Calcein AM in an Example of the invention of this application (A: 32D cell, B: Dead cell, I: bright field microscopy image, II: fluorescence microscopy image).

Images of transmission microscopy and fluorescence microscopy are shown in FIG. 3 (I: bright field image, II: fluorescence image).

From FIG. 3, the immobilization of 32D cells was confirmed (FIG. 3A). In addition, by the comparison with the images of dead cells (FIG. 3B), it was confirmed that the immobilized cells were living cells.

Comparative Example 1

Instead of Oleyl-O-PEG (4000)-NHS, by using PEG (5000)-NHS that does not contain Oleyl chain, 32D cells were immobilized by the same method as in Example 1.

Figure 4:
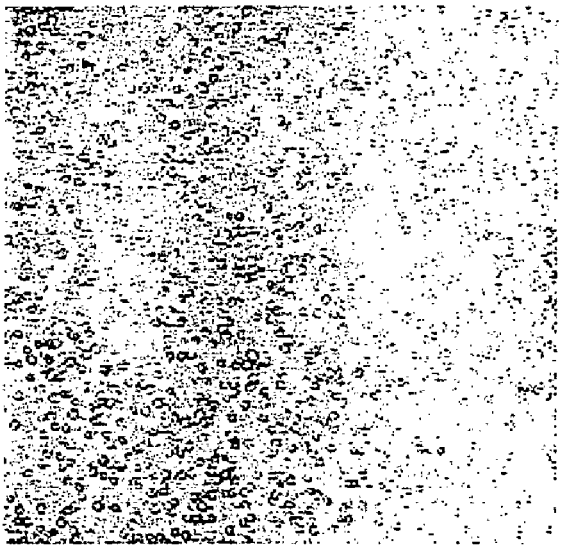
FIG. 4 shows photographs showing bright field microscopy images of 32D cells immobilized by the method of the invention of this application and 32D cells immobilized with the use of PEG (5000) which does not have Oleyl chain in an Example of the invention of this application (A: BSA/Oleyl-O-PEG (4000)-NHS, B: BSA/PEG (5000)).
Figure 4:

Bright field microscopy images are shown in FIG. 4B.

In the system using Oleyl-O-PEG (4000)-NHS (FIG. 4A), it was confirmed that 32D cells were immobilized in a living state. On the other hand, in the system using PEG (5000)-NHS without Oleyl chain (FIG. 4B), the immobilization of 32D cells was not observed.

These results indicate that for the immobilization of cells, a hydrophobic chain (Oleyl chain) is necessary.

Example 2

By the same method as in Example 1, an immobilization support was prepared by using Oleyl-O-PEG (8000)-NHS (PEG Mw: 8000 Da, n=180) instead of Oleyl-O-PEG (4000), and 32D cells were immobilized.

Comparative Example 2

BSA was adsorbed to a culture dish by the same method as in Example 2, but without adding Oleyl-O-PEG (8000)-NHS, and then a 32D cell solution ($1 \times 10^6$ cells/ml) was added directly and left to stand until the cells were precipitated on the surface of the solid phase, and the solid phase was washed with PBS.

Figure 5:
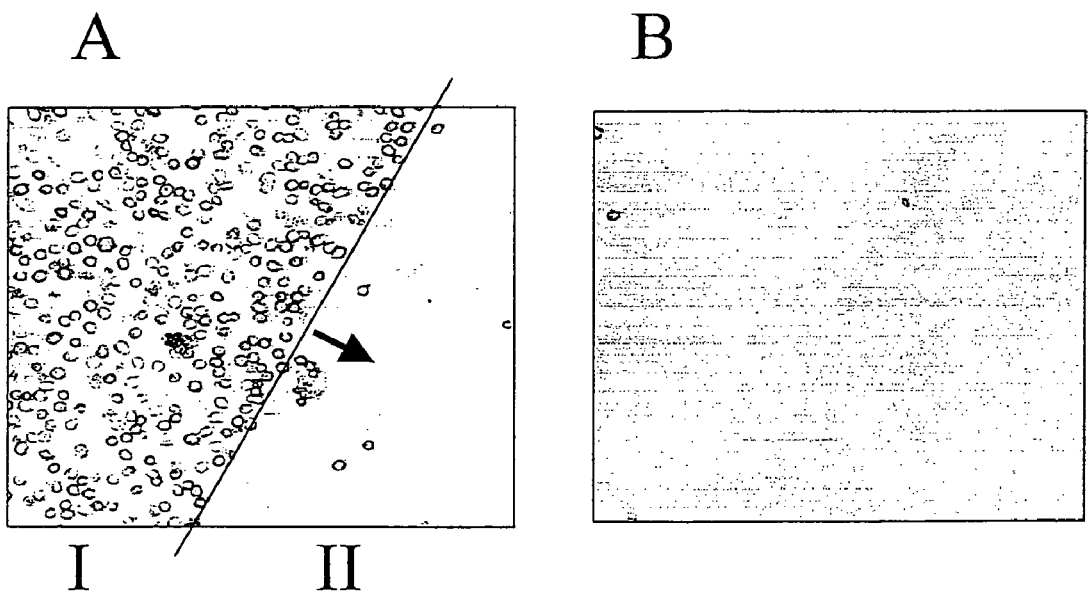
FIG. 5 shows photographs showing bright field microscopy images of 32D cells immobilized by the method of the invention of this application and 32D cells with which immobilization operation of cells was directly performed after causing BSA to be adsorbed to a culture dish in an Example of the invention of this application (A: BSA/Oleyl-O-PEG (2000)-NHS region (I) and BSA region (II), B: BSA).

In FIG. 5, bright field microscopy images of Example 2 and Comparative Example 2 are shown.

In the system in which Oleyl-O-PEG (8000)-NHS was bound to BSA (FIG. 5A-I), it was confirmed that the cells were immobilized on the immobilization support. On the other hand, in the region where Oleyl-O-PEG (8000)-NHS was not bound (FIG. 5A-II), the immobilization of cells was not observed.

Furthermore, in the case where the cells were added directly without binding Oleyl-O-PEG (8000)-NHS after BSA was adsorbed, it was confirmed that the cells were not immobilized (FIG. 5B). From these results, it was confirmed that Oleyl-O-PEG-NHS is effective as an immobilizing agent of cells regardless of the molecular weight of PEG.

Example 3

The same operation as in Example 1 was conducted using Oleyl-O-PEG (2000)-NHS (PEG Mw: 2000 Da, n=40) instead of Oleyl-O-PEG (4000)-NHS and 32D cells were immobilized.

Comparative Example 3

After Oleyl-O-PEG (2000)-NHS was directly bound to a culture dish without BSA being adsorbed, 32D cells were immobilized by the same operation as in Example 1 (2).

Further, after BSA was adsorbed, 32D cells were directly immobilized without Oleyl-O-PEG (2000)-NHS.

Furthermore, 32D cells were sedimented directly to a culture dish without conducting the adsorption of BSA or the binding of Oleyl-O-PEG (2000)-NHS.

Figure 6:
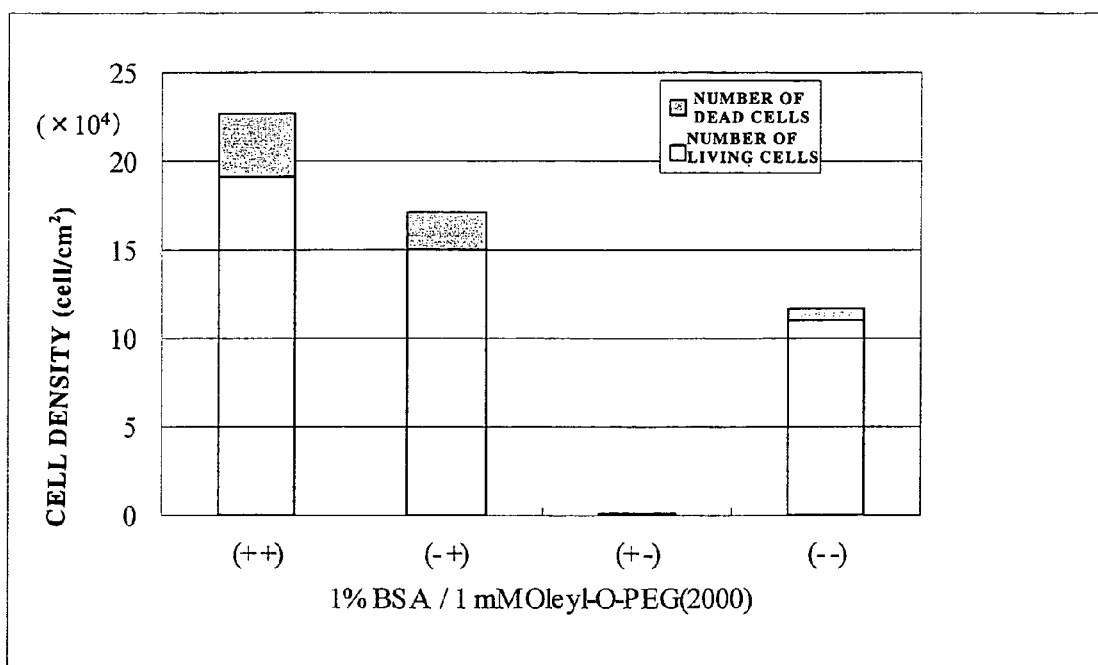
FIG. 6 is a graph showing cell densities of 32D cells immobilized by the method of the invention of this application, 32D cells immobilized by directly binding Oleyl-O-PEG (2000)-NHS to a culture dish without adsoring BSA and 32D cells directly immobilized after BSA is adsorbed in an Example of the invention of this application (black: number of dead cells, white: number of living cells).

The cell densities on the cell immobilization supports obtained in Example 3 and Comparative Example 3 were measured and are shown in FIG. 6.

From FIG. 6, it was confirmed that the cell density was the highest and the living cell density was also high when the BSA adsorption and the Oleyl-O-PEG (2000)-NHS binding were conducted (+/+). On the other hand, when 32D cells were directly immobilized after BSA was adsorbed without Oleyl-O-PEG (2000)-NHS (+/−), the cell immobilization was seldom observed and all of the observed cells were dead cells.

From these results, it is effective to use an immobilizing agent to immobilize living cells on a support at a high cell density, and it was confirmed that the method, in which Oleyl-O-PEG (2000)-NHS was bound after BSA had been adsorbed to the surface of a support, thereby immobilizing a cell, particularly was highly effective.

Example 4

By the same method as in Example 2, an immobilization support was prepared and human leukemia cells (K562) were immobilized by using a suspension of $1 \times 10^6$ cells/ml K562 cells instead of 32D cells.

Comparative Example 4

Further, by the same method as in Example 4, BSA was adsorbed to a culture dish, and a K562 cell solution ($1 \times 10^6$ cells/ml) was added without adding Oleyl-O-PEG (8000)-NHS and left to stand until the cells were precipitated on the surface of the immobilization support, and the solid phase was washed with PBS.

Figure 7:
FIG. 7 shows photographs showing bright field microscopy images of human leukemia cells (K562) cells immobilized by the method of the invention of this application and K562 cells directly immobilized after causing BSA to be adsorbed to a culture dish in an Example of the invention of this application (A: BSA/Oleyl-O-PEG (2000)-NHS, B: BSA).
Figure 7:
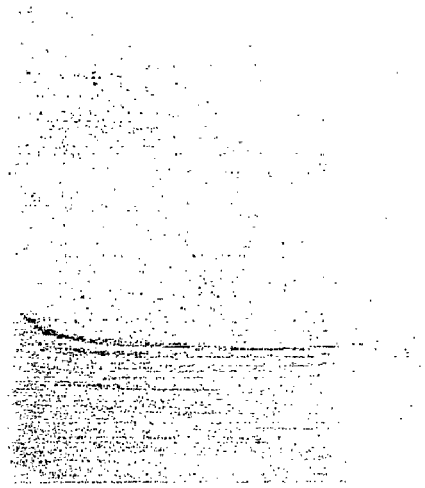

In FIG. 7, bright field microscopy images of Example 4 and Comparative Example 4 are shown.

From FIG. 7, it was confirmed that living cells were immobilized on the immobilization support on which Oleyl-O-PEG (8000)-NHS bound to BSA (FIG. 7A). On the other hand, it was confirmed that cells were not immobilized in the case where Oleyl-O-PEG (8000)-NHS was not bound after BSA was adsorbed (FIG. 7B).

From these results, it was confirmed that the cell immobilization method of the invention of this application is applicable to a human cell.

Example 5

By the same method as in Example 1, an immobilization support was prepared by using Oleyl-O-PEG (4000)-NHS (PEG Mw: 4000 Da, n=90), and as a non-adherent cell, both human B cell lymphoma Daudi and human T cell lymphoma Jurkat were respectively immobilized.

Similarly, as an adherent cell, mouse fibroblast cell NIH3T3, human embryonic kidney cell HEK293, and mouse ES cells derived from 129SV line were immobilized.

In both the non-adherent cells and the adherent cells, the immobilization on the surface of the immobilization support occurred within several minutes. Accordingly, it was confirmed that, by the cell immobilization method of the invention of this application, immobilization independent of the adhesion inherent to the cell becomes possible.

Figure 8:
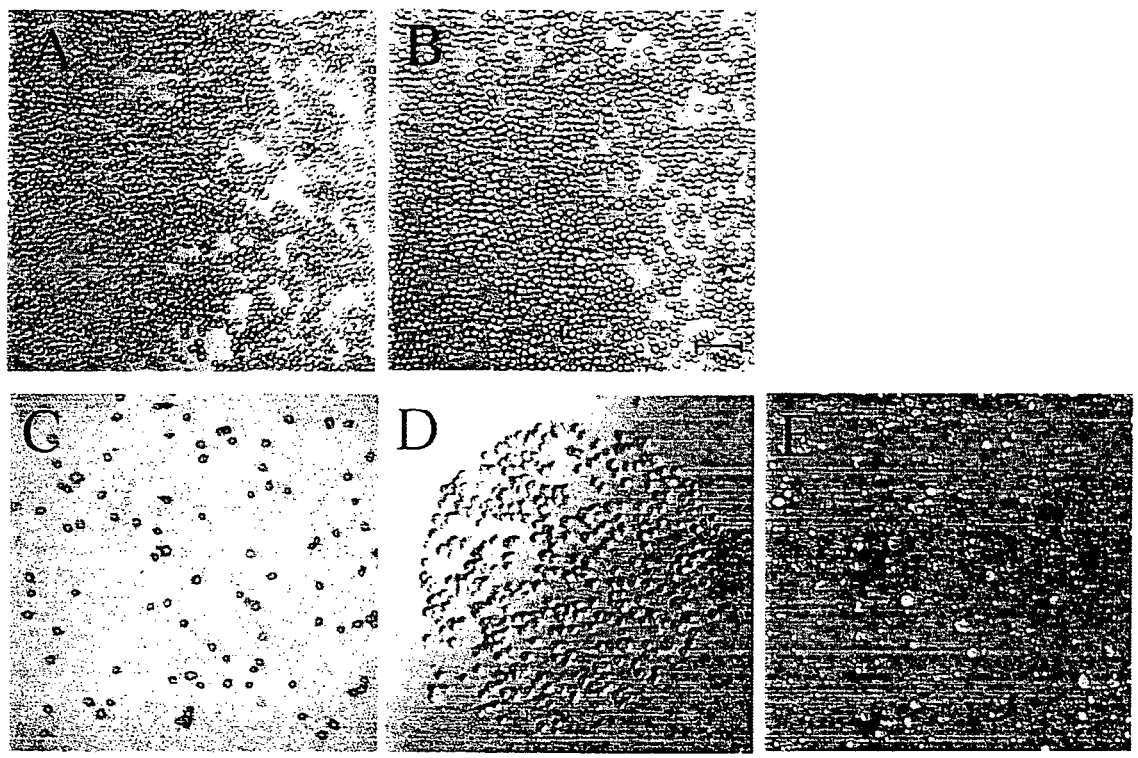
FIG. 8 shows photographs showing bright field microscopy images of various kinds of non-adherent cells and adherent cells immobilized by the method of the invention of this application in an Example of the invention of this application (A: human B cell lymphoma Daudi, B: human T cell lymphoma Jurkat, C: mouse fibroblast cell NIH3T3, D: human embryonic kidney cell 293, E: mouse ES cell).

In FIG. 8, bright field microscopy images of Example 5 are shown. Although the number of immobilization became sparse (FIG. 8C) when the added amount of cells was small, immobilization was confirmed in all of the cells. In addition, when Oleyl-O-PEG (4000)-NHS was bound in a circular form with the diameter of about 500 μm, cells were immobilized in the corresponding circular form (FIG. 8D). From these results, it was confirmed that in the case of adherent cells as well, by the method of the invention of this application, immobilization at a desired location independent of the structure of the cell becomes possible.

2. Gene Introduction into Cell

Example 6

By the same method as in Example 5, an immobilization support was prepared by using Oleyl-O-PEG (4000)-NHS, and a small amount (about 0.1 to 1 μL) of the following gene mixture solution was spotted on the surface, dried out, and solidified.

Thereon, cells suspended in PBS or serum-free RPMI1640 medium were added, and left to stand at room temperature for 30 minutes to immobilize cells. After cells which had not been immobilized were washed with PBS and removed, the culture solution was replaced with 10% FBS added RPMI1640 medium and the culture was carried out at 37° C. for 24 to 72 hours.

Gene Mixture Solution

| | |
|---|---|
| Lipofectamine 2000 (Invitrogen) | 2 μL |
| 1 μg/μL pDsRed2-N1 (Clontech) | 4 μL |
| RPMI1640 (Serum free; Asahi Technoglass) | 4 μL |
| Water | 10 μL |
| Total volume | 20 μL |

Figure 9:
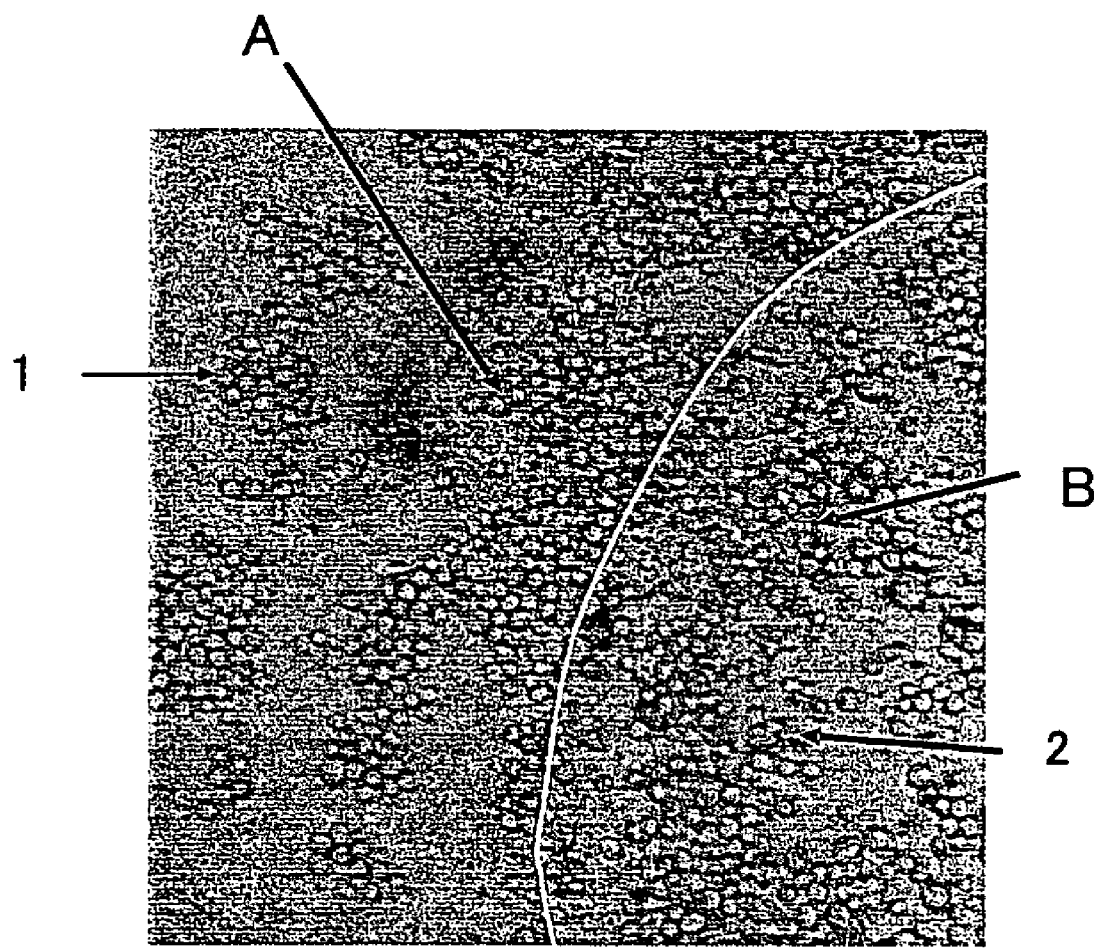
FIG. 9 shows a photograph showing a superimposed image of the bright field microscopy image and the fluorescence image of K562 cells, with which gene introduction and immobilization were performed by the method of the invention of this application in an Example of the invention of this application (A: region where a gene mixture solution was not spotted, B: region where a gene mixture solution was spotted, Whole surface: surface of immobilization support with the use of Oleyl-O-PEG-NHS, 1: K562 cells, 2: red fluorescence protein DsRed2 (red) genetically expressed).

In FIG. 9, a image superimposing the bright field microscopy image and the fluorescence image of cells after 48 hours from the start of culture is shown. Because the fluorescence of red fluorescence protein was observed only in the region where the gene mixture solution was spotted, it was confirmed that, by the gene introduction method of the invention of this application, immobilization of cells and gene introduction can be carried out simultaneously by using a commercially available reagent for gene introduction.

In this method, it was revealed that a gene mixture solution spotted on Oleyl-O-PEG was not diffused by drying out and solidifying the gene mixture solution, and further that cells which were immobilized at the region where a gene mixture solution had been spotted, incorporated that gene.

3. Solid Phase Culture for Cell

Example 7

On an Oleyl-O-PEG (4000)-NHS spot (about 1 mm in diameter), about one-third the amount of the confluent state (about 3000 cells/mm$^2$) of mouse myelocytic leukemia cell 32D and human erythroleukemia cell K562, which had been suspended in PBS, were added and left to stand at room temperature for 10 minutes, and the cells were immobilized. Then, by washing with PBS, cells which had not been immobilized were removed. The medium was replaced with 10% FBS added RPMI1640 medium and the immobilized cells were cultured at 37° C. for certain periods.

Figure 10:
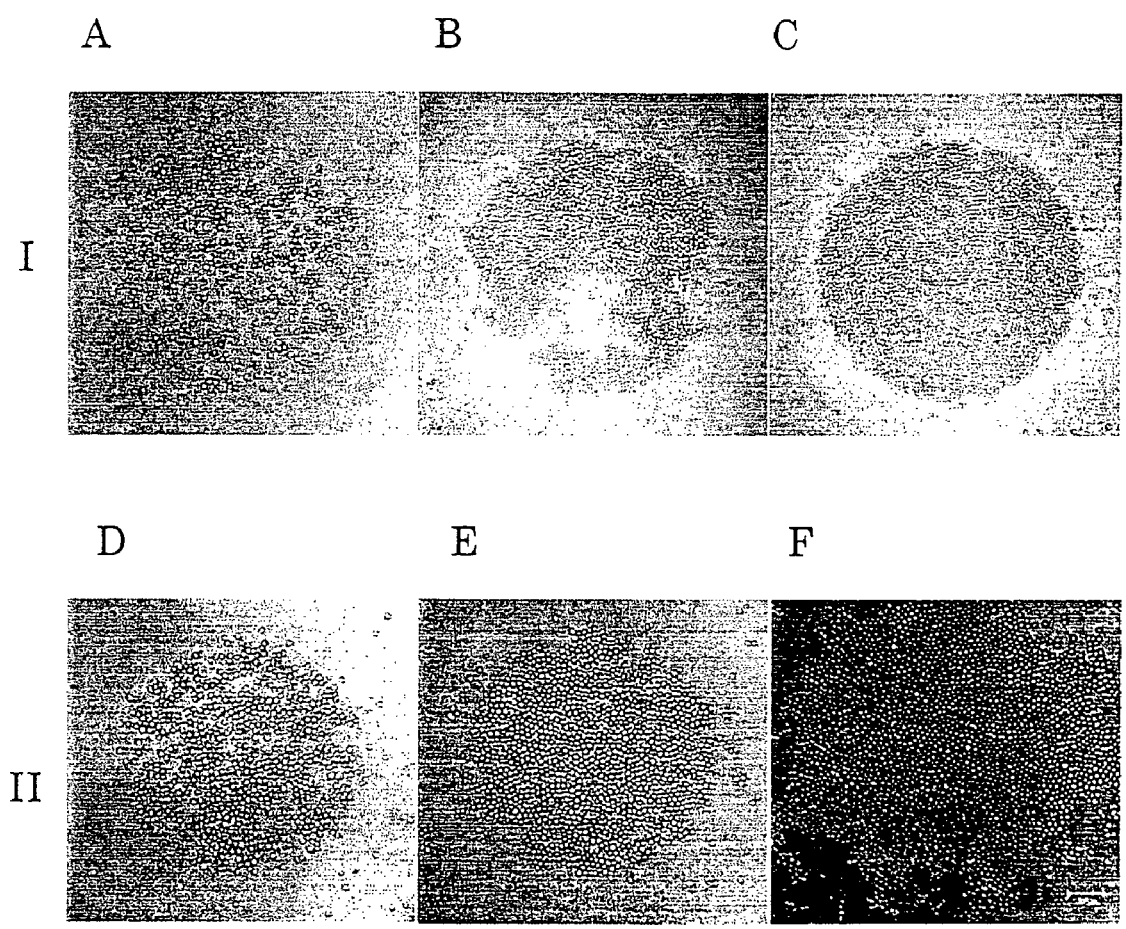
FIG. 10 shows photographs showing bright field microscopy images (and a fluorescence image), for each culture period, of 32D cells and K562 cells immobilized by the method of the invention of this application in an Example of the invention of this application (I: 32D cells, II: K562 cells, A: at the start of culture, B: after 2 days, C: after 3 days, D: after 0 days, E: after 3 days, F: fluorescence image after 7 days).

In FIG. 10, bright field microscopy images (and a fluorescence image) of each immobilized cell for each culture period are shown.

When 32D cells were cultured for 3 days, it was confirmed that the cells grew until they were confluent only on the Oleyl-O-PEG (4000)-NHS spot. In addition, regarding K562 cells, similarly, it was confirmed that the cells grew until they were confluent only on the Oleyl-O-PEG (4000)-NHS spot by culturing for 3 days. Both cells were confirmed to be alive until the fourth day.

The culture was further continued and the survival rate of cells cultured for 7 days was investigated by using Calcein AM. It was confirmed that all immobilized cells were alive. Although non-specific adhesion of cells to the region other than the Oleyl-O-PEG (90)-NHS spot was observed after culturing for 7 days, this was due to the nature of K562 cells and was not a phenomenon resulting from the Oleyl-O-PEG-NHS immobilization. In addition, in the immobilized K562 cells cultured for 7 days, differentiation or apoptosis was not observed.

K562 is an undifferentiated cell and it has been known to differentiate into an erythroblast or a megakaryoblast by the mitogen-activated protein (MAP) signal or the protein kinase C (PKC) and calcium signal, respectively. However, because neither differentiation nor apoptosis was observed, it was shown that the MAP, PKC and calcium signals or an apoptosis related signal are not affected by the immobilization method of the invention of this application.

Example 8

Gene mixture solutions were prepared for two kinds of genes, pME-EGFP, which is an enhanced green fluorescence protein (EGFP) expression vector, and pDsRed2-N1 (Clontech), which is a red fluorescence protein gene expression vector, and were spotted respectively at a distance of about 500 μm separated from each other on the inside surface of the same container that was used as an immobilization support (diameter: about 1 mm, mixture solution amount: about 0.3 μl). It was investigated if the respective gene expressing cells would be immobilized only on the defined location or if cross-contamination, in which the expressing cells are dispersed and move to another spot, would be caused.

Figure 11:
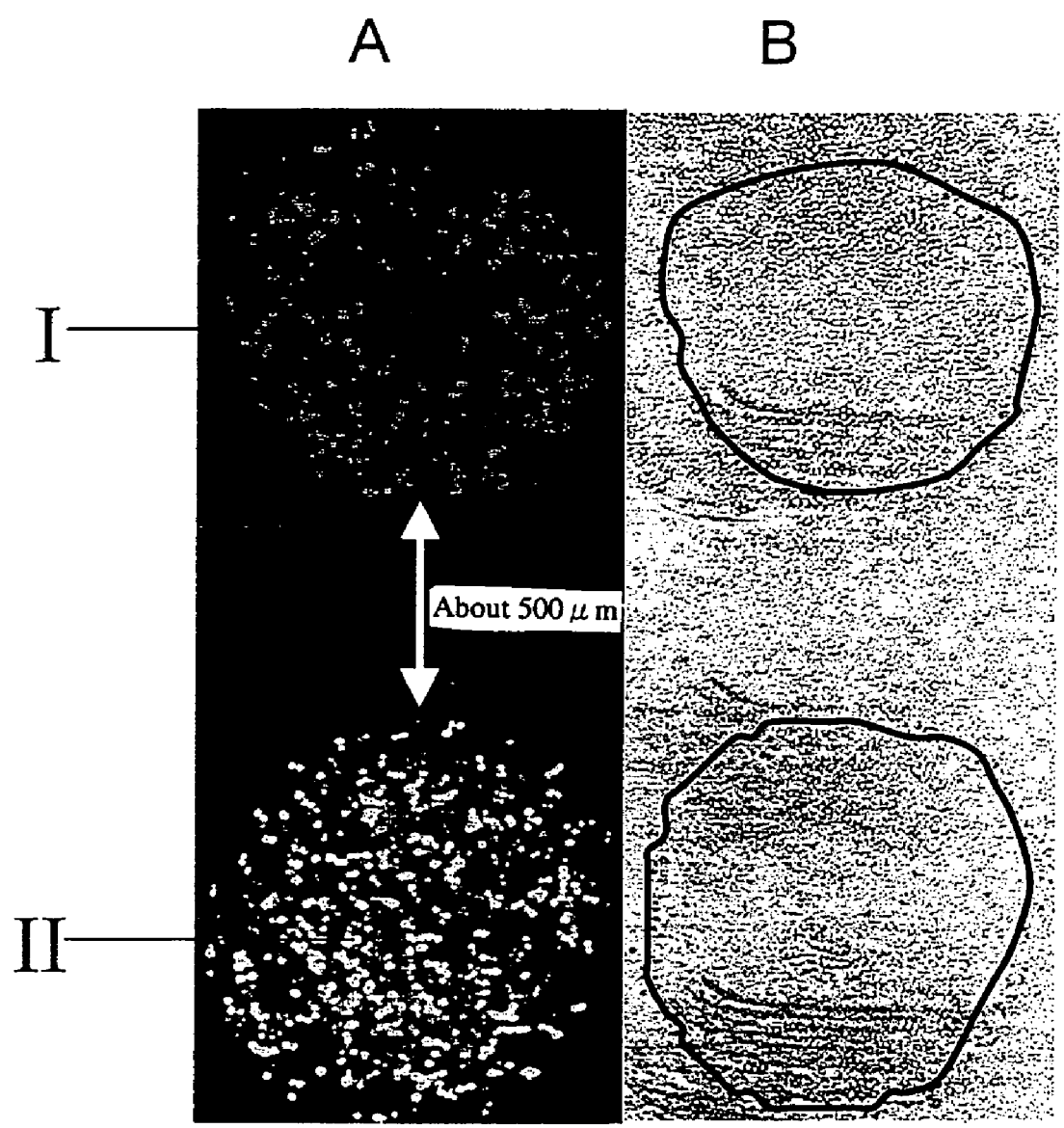
FIG. 11 shows photographs showing fluorescence images and bright field images of two kinds of gene expressing cells immobilized at a distance of about 500 μm separated from each other by the method of the invention of this application after 48 hours in an Example of the invention of this application. It indicates that each gene expressing cell is immobilized only at a defined location and cross contamination does not occur (A: pDsRed2-N1, B: pME-EGFP, I: fluorescence image, II: bright field image).

In FIG. 11, fluorescence images and bright field images of each spot after 48 hours from the start of culture are shown. From these results, it was confirmed that the two kinds of genes were immobilized only on the defined regions respectively, and it was shown that cross-contamination is not caused in the solid phase culture method for a cell of the invention of this application.

Example 9

An immobilization support was prepared by using Oleyl-O-PEG (4000)-NHS, a pDsRed2-N1 gene mixture solution was spotted on its surface, and HEK293 was then also immobilized thereon. Above these immobilized HEK293 cells, the following gel solution was added (so that the thickness after gelation was about 500 μm) and gelated by heating at 37° C. for 30 minutes.

Gel Solution

| Cellmatrix type I-A (Nitta Gelatin Inc.) | 700 μL |
|---|---|
| 5-fold concentrated DMEM | 200 μL |
| 2.2% sodium hydrogen carbonate/ 200 mM HEPES/0.05 N NaOH solution | 100 μL |

An appropriate amount of 10% FBS added DMEM was added on the obtained gel and incubated in a $CO_2$ incubator at 37° C. for 72 hours under heating.

Figure 12:
FIG. 12 shows photographs showing a confocal three-dimensional image and a confocal three-dimensional transmission image of HEK293 cells immobilized by the method of the invention of this application when gel embedding culture was performed in an Example of the invention of this application (A: confocal three-dimensional image, B: confocal three-dimensional transmission image).
Figure 12:
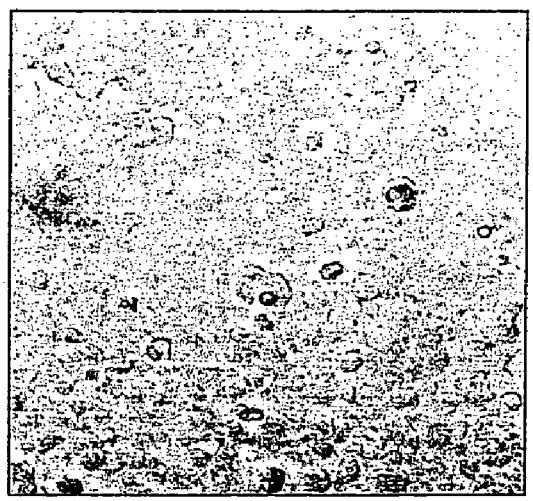

In FIG. 12, a confocal fluorescence three-dimensional image and a confocal three-dimensional transmission image of the immobilized HEK293 cells are shown. From these results, it was confirmed that the cells immobilized in the gel are also capable of being grown and red fluorescence protein is expressed in the cells immobilized on the gene spot.

Example 10

On the surface of Oleyl-O-PEG, immobilization was conducted while a small interfering RNA (siRNA) was being introduced into cells.

First, after an immobilization support was prepared by using Oleyl-O-PEG (8000)-NHS (PEG Mw: 8000 Da, n=180), 0.1 to 1 μL of the siRNA mixture solution shown below was spotted, dried out, and solidified.

K562 cells suspended in serum-free RPMI1640 medium were added thereon, left to stand at 4° C. for 10 minutes, and immobilized. After cells which had not been immobilized were washed with PBS and removed, the medium was replaced with 10% FBS added RPMI1640 medium and incubated at 37° C. for 4 hours in a $CO_2$ incubator, and after that, observation was carried out using a confocal laser-scanning microscope.

siRNA Mixture Solution

| Lipofectamine 2000 (Invitrogen) | 2 μL |
|---|---|
| 0.15 μg/μL FITC labeled siRNA (QIAGEN) | 13.3 μL |
| RPMI1640 (Serum free) | 4 μL |
| Water | 0.7 μL |
| Total volume | 20 μL |

Figure 13:
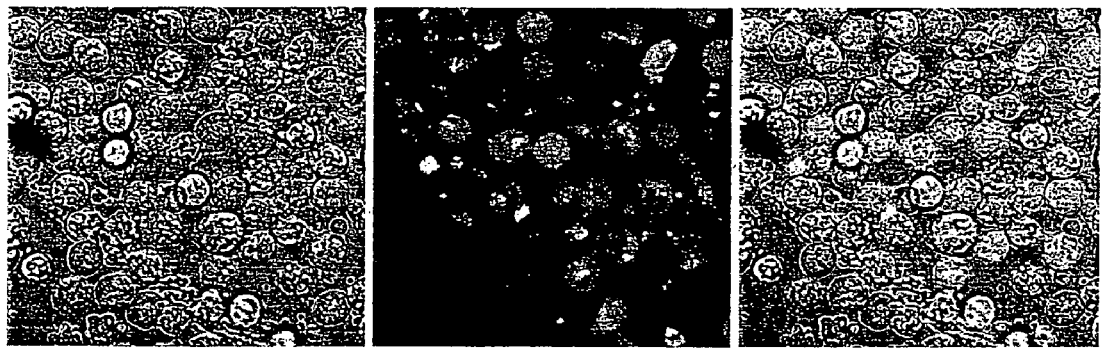
FIG. 13 shows photographs showing a confocal bright field image, a confocal fluorescence image and a superimposed image of these images of HEK293 cells with which introduction of siRNA and cell immobilization were performed by the method of the invention of this application in an Example of the invention of this application (A: confocal bright field image, B: confocal fluorescence image, C: superimposed image of A and B).

In FIG. 13, a bright field image, a confocal fluorescence image, and a superimposed image of these images are shown. Because cells in which fluorescence was observed were observed only on the siRNA mixture solution spot, it was shown that, by applying the method of the invention of this application, siRNA can be introduced only into a cell immobilized on a specific location.

4. Immobilization of Liposome

Example 11

(1) Preparation of Liposome Entrapment of Fluorescein
Three kinds of liposomes entrapment of fluorescein were prepared by adding cationic liposome (EL-C-01; Nippon Oil & Fats Co., Ltd.), weakly negatively charged liposome (EL-N-01; Nippon Oil & Fats Co., Ltd.) and anionic liposome (EL-A-01; Nippon Oil & Fats Co., Ltd.) to separate vials, adding 2 ml of 0.2 mM 5-(aminomethyl)-fluorescenin (fluorescent material) to each of the vials, and gel-filtrating with PBS by using PD-10 (Amersham Pharmacia Biotech).

The lipid amount in each liposome suspension was set at 0.0125 mmol/ml.

(2) Preparation of Oleyl-O-PEG (4000) Immobilization Support

To the glass part of a glass bottom dish produced by MatTek (No.0, non-coated), 0.1 ml of 1% BSA was added and left at 4° C. overnight. After it was washed with PBS 3 times, 0.1 ml of 0.1 mM Oleyl-O-PEG (4000)-NHS was added, and it was washed with PBS after being left at room temperature for 1 hour.

(3) Immobilization of Liposome

To three Oleyl-O-PEG (4000) immobilization glass bottom dishes, 0.1 ml of each of the liposomes enclosed in fluorescein was added and left at room temperature for 15 minutes. After they were washed with PBS 4 times, 1 ml of PBS was added.

They were observed with a confocal laser-scanning microscope.

Comparative Example 5

By the same method as in Example 5, after BSA was adsorbed to a glass bottom dish, liposome was directly immobilized without binding to Oleyl-O-PEG (4000), and an evaluation was carried out in the same manner.

Figure 14:
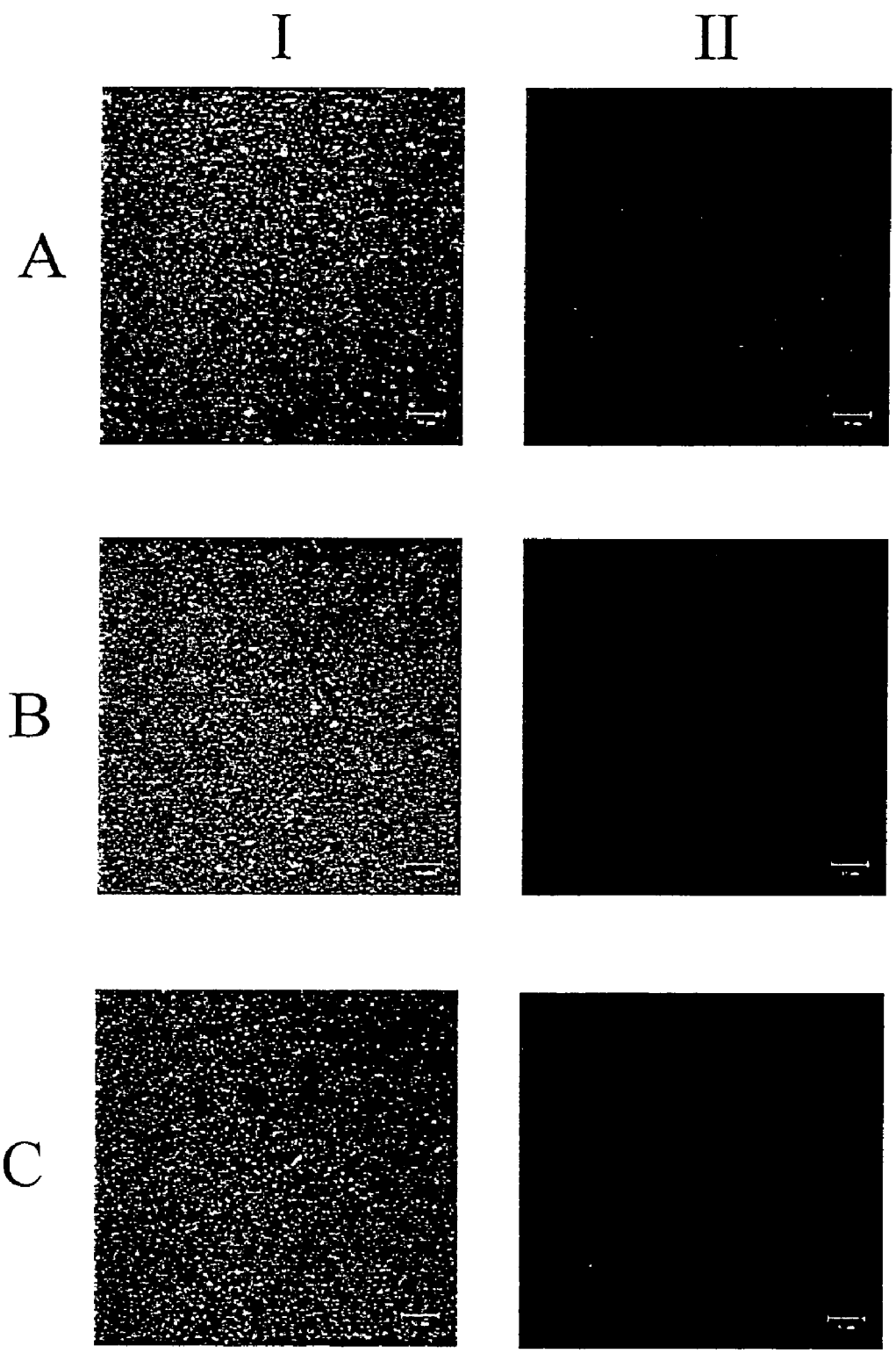
FIG. 14 shows photographs showing bright field microscopy images of immobilized liposomes and liposomes for comparison which were directly immobilized after BSA was caused to adsorb to a culture dish, as in an Example of the invention of this application (A: cationic liposome, B: weakly negatively charged liposome, C: anionic liposome, I: BSA/Oleyl-O-PEG (4000), II: BSA).

Microscopy images of Example 5 and Comparative Example 5 are shown in FIG. 14.

It was confirmed that the cationic liposome (FIG. 14A), the weakly negatively charged liposome (FIG. 14B) and the anionic liposome (FIG. 14C) all were immobilized when Oleyl-O-PEG (4000) was used (FIG. 14I).

On the other hand, when the liposome was added directly to the glass bottom dish having BSA adsorbed without binding Oleyl-O-PEG (4000), none of the liposomes were immobilized (FIG. 14II).

5. Immobilization of *E. coli*

Example 12

In the same manner as in Example 1, an immobilization support was prepared by using Oleyl-O-PEG (2000) and GST-EGFP expressing *E. coli* was immobilized on the surface.

Figure 15:
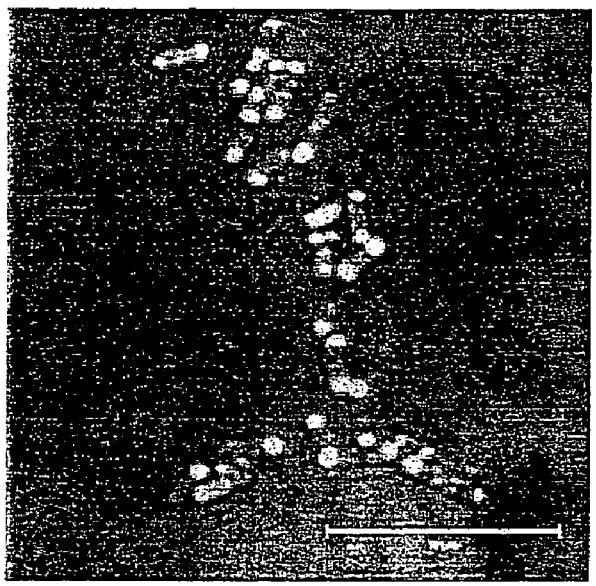
FIG. 15 shows photographs showing (A) a superimposition of the bright field image and the fluorescence image, (B) a fluorescence image, which show GST-EGFP expression $E.\ coli$ immobilized on Oleyl-O-PEG (2000) solid phase glass.
Figure 15:
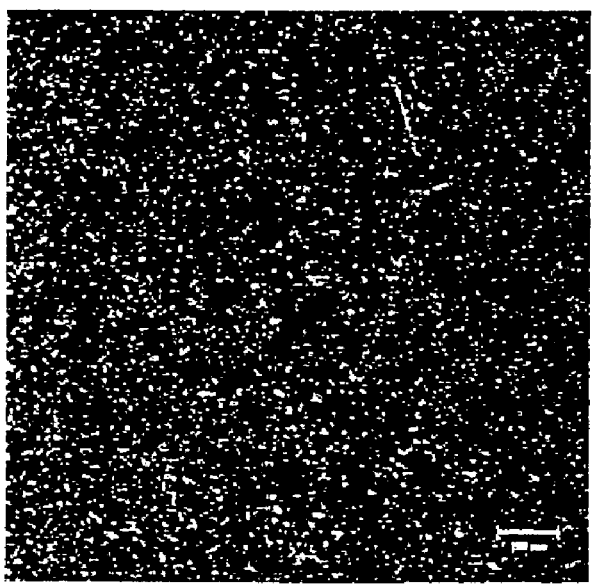

FIG. 15(A) shows the result, superimposing the bright field image and the fluorescence image, and FIG. 15(B) shows a fluorescence image.

From this, the immobilization of *E. coli* was confirmed.

ADVANTAGE OF THE INVENTION

As described in detail above, by the invention of this application, a convenient method for immobilizing a living cell or a liposome to a support at a high density is provided. The immobilization method for a cell and a liposome of this invention is a highly versatile method which is applicable not only to an adherent cell, but also to a floating cell or a phospholipid vesicle. In addition, by the invention of this application, a method for introducing a gene into a cell immobilized on a support or a method for culturing an immobilized cell are also provided. By applying these methods, construction of cell devices such as a cell sensor, a cell microarray and a microreactor, elucidation of the mechanism of the high order tissue formation of cells, regenerative medicine, growth of hematopoietic stem cells or the like becomes possible, therefore, the invention of this application has a high usefulness in many fields.

The invention claimed is:

1. A cell immobilization material, wherein a cell is immobilized on a support having an immobilizing agent bound to the main body of the support, the immobilizing agent being a straight chain compound that consists of a hydrophobic chain of a saturated or unsaturated hydrocarbon chain whose carbon number is in a range of 6 to 22, and a hydrophilic chain of a polyethylene glycol, and wherein the hydrophilic chain in the immobilizing agent has an active ester group at its end, and wherein the immobilizing agent is polyethyleneoxide-oleyl ether-N-hydroxysuccinimide ester.

2. The cell immobilization material according to claim 1, wherein the immobilizing agent is fixed to the main body of the support on which a protein is adsorbed.

* * * * *